United States Patent [19]

Remington

[11] Patent Number: 4,963,531
[45] Date of Patent: Oct. 16, 1990

[54] AZITHROMYCIN AND DERIVATIVES AS ANTIPROTOZOAL AGENTS

[75] Inventor: Jack S. Remington, Menlo Park, Calif.

[73] Assignee: Pfizer Inc., New York, N.Y.

[21] Appl. No.: 359,676

[22] PCT Filed: Sep. 10, 1987

[86] PCT No: PCT/US87/02317

§ 371 Date: Aug. 16, 1988

§ 102(e) Date: Aug. 16, 1988

[87] PCT Pub. No: WO89/02270

PCT Pub. Date: Mar. 23, 1989

[51] Int. Cl.$^5$ .................. A61K 31/70; A61K 31/71
[52] U.S. Cl. ...................... 514/29; 536/7.2; 536/7.4
[58] Field of Search ............... 536/7.4, 7.2; 514/29

[56] References Cited

U.S. PATENT DOCUMENTS

| | | | |
|---|---|---|---|
| 4,474,768 | 10/1984 | Bright | 536/7.4 |
| 4,512,982 | 3/1985 | Hauske et al. | 536/7.2 |
| 4,517,359 | 5/1985 | Kobrehel et al. | 536/7.4 |
| 4,526,889 | 7/1985 | Bright | 536/7.2 |

OTHER PUBLICATIONS

Hofflin et al., Antimicrobial Agents and Chemotherapy, v. 31, pp. 346-348, (1987)(b).

*Primary Examiner*—John W. Rollins
*Assistant Examiner*—W. Catchpole
*Attorney, Agent, or Firm*—Peter C. Richardson

[57] ABSTRACT

A method of use of azithromycin or derivatives of azithromycin in the treatment of infection caused by *Toxoplasma gondii* in mammals is disclosed.

5 Claims, No Drawings

AZITHROMYCIN AND DERIVATIVES AS ANTIPROTOZOAL AGENTS

BACKGROUND OF THE INVENTION

The present invention is directed to the use of compounds of the formula (I) as defined below, viz., azithromycin, its 4″-epimer, and corresponding 4″-deoxy-4″-amino analogs in the treatment of systemic protozoal infections in mammals, particularly in the treatment of toxoplasmosis, a protozoal infection due to strains of *Toxoplasma gondii*, particularly troublesome in pregnant women and among those such as AIDS patients, who are immune deficient.

Azithromycin is the U.S.A.N. (generic name) for 9a-aza-9a-methyl-9-deoxo-9a-homoerythromycin A, a broad spectrum antibacterial compound derived from erythromycin A. Azithromycin was independently discovered by Bright, U.S. Pat. No. 4,474,768 and Kobrehel et al., U.S. Pat. No. 4,517,359. The name "N-methyl-11-aza-10-deoxo-10-dihydroerythromycin A" was employed in these patents. The present more systematic name is based upon the ring expansion and replacement nomenclature of the "IUPAC Nomenclature of Organic Chemistry, 1979 Edition," Pergamon Press, 1979, pp. 68–70, 459, 500–503. 4″-Epi-azithromycin (4″-epi-9a-aza-9a-methyl-9-deoxo-9a-homoerythromycin A), 4″-amino-4″-deoxy-azithromycin (4″-amino-9a-aza-9a-methyl-9-deoxo-4″-deoxy-9a-homoerythromycin A), and 4″epi-4″-amino-4″-deoxyazithromycin A (4″-epi-4″-amino-9a-aza-9a-methyl-9-deoxo-4″-deoxy-9a-homoerythromycin A), also broad spectrum antibacterials derived from erythromycin A, are the subjects of Bright, U.S. Pat. No. 4,526,889, Hauske and Nagel, U.S. Pat. No. 4,512,982, and Hauske and Nagel, loc. cit., respectively.

There is a continuing need for drugs which are effective against protozoal infections in mammals, in particular against toxoplasmosis in man. Transmission of the disease may occur transplacentally, by ingestion of raw or undercooked meat containing tissue cysts, or by exposure to oocysts in cat feces. Neonatal congenital toxoplasmosis, which is acquired transplacentally, the mother having acquired a primary infection during or prior to pregnancy, can lead to spontaneous abortion, miscarriage or still-birth, birth defects, or the birth of a child with the clinical disease. The disease can cause brain damage and even death in those having weakened immune systems, particularly among those suffering from AIDS (acquired immune deficiency syndrome) where toxoplasma encephalitis is a commonly found, life threatening infection. Heretofore, there has been no alternative to the present regimen of pyrimethamine plus a sulfonamide—a relatively toxic regimen with numerous side effects among the latter patient population. Approximately 20% of AIDS patients are seropositive for Toxoplasma antibodies and approximately 30% of these seropositive individuals will suffer toxoplasmic encephalitis, reflecting the critical problem in this patient population. In one recent series, approximately 50% of the patients died, median time to death being 4 months. Furthermore, since the incidence of relapse is also prohibitively high, new drugs are needed which can be given both for initial treatment and as suppressive therapy for the life of the patient.

It has recently been reported that the macrolide antibiotic, roxithromycin (the 9-[O-(2-methoxyethoxymethyl)]oxime of erythromycin A) possesses activity against toxoplasmosis in mice (see Hofflin and Remington, Antimicrobial Agents and Chemotherapy, vol. 31, pp. 346–348 (1987); and leading references there cited).

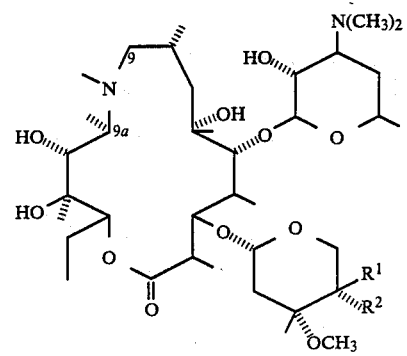

(Ia) $R^1$=OH, $R^2$=H azithromycin
(Ib) $R^1$=H, $R^2$=OH 4″-epi-azithromycin
(Ic) $R^1$=$NH_2$, $R^2$=H 4″-amino-4″-deoxy-azithromycin
(Id) $R^1$=H, $R^2$=$NH_2$ =4″-epi-4″-amino-4″-deoxy-azithromycin

SUMMARY OF THE INVENTION

We have now found that the compounds of the formula (I), wherein one of $R^1$ and $R^2$ is hydrogen and the other is hydroxy or amino (conveniently named herein as azithromycin derivatives, vide supra) possess remarkably potent activity against Protozoa, particularly Toxoplasma species, and so are valuable in pharmaceutical compositions for a method of treating or preventing protozoal infections in mammals, including man. These compounds are especially valuable in the treatment of toxoplasmosis, an infection due to a strain of *Toxoplasma gondii*, which, as noted above, is a particular problem in pregnant women and in immune compromised patients.

DETAILED DESCRIPTION OF THE INVENTION

The present invention is readily carried out. The compounds of the formula (I) are prepared according to the methods of U.S. Pat. Nos. 4,474,768, 4,512,982 and 4,526,889, cited above, which are hereby included by reference. A particularly valuable form of azithromycin (Ia) for this purpose is azithromycin dihydrate prepared according to methods disclosed in Examples below.

The utility of the compounds of the formula (I) in the treatment or prevention of protozoal infections in mammals is demonstrated by their remarkable activity in model *Toxoplasma gondii* infections in mice. For example, we have found azithromycin (Ia) to have potent in vivo activity against murine toxoplasmosis. Mice infected intraperitoneally with $10^2$ tachyzoites of the virulent RH strain of *T. gondii* and treated 24 hours later with 200 mg azithromycin kg/day orally by gavage (solubilized in polyethylene glycol 200) for 10 days all survived. Concentrations of 100 or 50 mg/kg resulted in 80 and 20% survival, respectively. Further experiments revealed that one daily dose of 200 mg/kg for each of 3 days after infection resulted in 100% survival of mice infected with $10^3$ RH tachyzoites. Moreover, this concentration of the drug protected 100% of infected mice when administered as late as 72 hours after infection with $10^2$ RH tachyzoites. Additional experiments revealed that 70% of mice infected intracerebrally with $10^4$ tachyzoites of the C56 strain of *T. gondii* and treated with 200 mg/kg/day for 10 days survived, but only 10% of untreated controls survived. These results indicate that azithromycin is highly effective against infection with *T. gondii*. (See Hofflin et al., cited above, and references there cited, for more detailed descriptions of these murine toxoplasmosis models).

In the treatment or prevention of systemic protozoal infections in mammals, particularly toxoplasmosis in man due to strains of *Toxoplasma gondii*, the compounds of the formula (I), including the pharmaceutically acceptable salts thereof, are dosed orally or parenterally. Oral dosage will generally be preferred, particularly in cases where the drug is dosed chronically as a preventive measure. However, particularly in acute administration for severe cases of toxoplasmosis, parenteral administration may be preferred, a matter to be determined at the discretion of the attending physician. The preferred dosage range is about 5-100 mg per kg of body weight per day, in single or divided daily doses, regardless of the route of administration. In special situations, particularly in life-threatening cases of infection, higher doses may be prescribed at the discretion of the attending physician.

When used to treat or prevent a systemic protozoal infection in a mammal, particularly toxoplasmosis in man, the compounds of the formula (I), including the pharmaceutically acceptable salts thereof, can be dosed alone, but are preferably dosed in the form of pharmaceutical compositions comprising the active compound and a pharmaceutically-acceptable carrier or diluent. Such pharmaceutical compositions, whether for oral or parenteral administration, are prepared according to conventional methods of pharmacy, for example, as disclosed in U.S. Pat. Nos. 4,474,768, 4,512,982 and 4,526,889, cited above, and included by reference.

The present invention is illustrated by the following example, but is not limited to the details thereof.

EXAMPLE 1

Non-Hygroscopic Azithromycin Dihydrate Method A

The hygroscopic monohydrate of Preparation 1 (100 g; water-content:3.1%), tetrahydrofuran (220 ml) and diatomaceous earth (5 g) were combined in a 500 ml Erlenmyer flask, stirred for 30 minutes and filtered with 20 ml of tetrahydrofuran wash. The combined filtrate and wash was transferred to a 3 liter round bottom flask. The solution was stirred vigorously and $H_2O$ (2.0 ml) was added. After 5 minutes, hexane (1800 ml) was added over 5 minutes, with continued vigorous stirring. Following an 18 hour granulation period, title product was recovered by filtration with $1 \times 10$ ml hexane wash, and dried in vacuo to $4.6 \pm 0.2\%$ $H_2O$ by Karl Fischer, 89.5 g.

Method B

The hygroscopic monohydrate of Preparation 1 (197.6 g) and tetrahydrofuran (430 ml) were charged to a reactor and the mixture stirred to achieve a milky white solution. Activated carbon (10 g) and diatomaceous earth (10 g) were added and the mixture stirred for 15 minutes, then diluted with 800 ml of hexane and filtered with suction over a pad of diatomaceous earth with 250 ml of hexane for wash. The combined filtrate and wash was diluted to 2500 ml with hexane and warmed to 34° C. With stirring, 24.7 ml of $H_2O$ was added. The mixture was allowed to cool to room temperature, granulated for five hours and title product recovered and dried as in Method A, 177.8 g.

The dihydrate melts sharply at 126° C. (hot stage, 10°/minute); differential scanning calorimetry (heating rate, 20° C./minute) shows an endotherm at 127° C.; thermal gravimetric analysis (heating rate 30° C./minute) shows a 1.8% weight loss at 100° C. and a 4.3% weight loss at 150° C.; ir (KBr) 3953, 3553, 3488, 2968, 2930, 2888, 2872, 2827, 2780, 2089, 1722, 1664, 1468, 1426, 1380, 1359, 1344, 1326, 1318, 1282, 1270, 1252, 1187, 1167, 1157, 1123, 1107, 1082, 1050, 1004, 993, 977, 955, 930, 902, 986, 879, 864, 833, 803, 794, 775, 756, 729, 694, 671, 661, 637, 598, 571, 526, 495, 459, 399, 374, 321 and 207 $cm^{-1}$; $[alpha]_D^{26} = -41.4°$ (c=1, $CHCl_3$)

Anal Calcd. for $C_{38}H_{72}N_2O_{12} \cdot 2H_2O$:

C, 58.14; H, 9.77; N, 3.57; $OCH_3$, 3.95; $H_2O$, 4.59.

Found:

C, 58.62; H, 9.66; N, 3.56; $OCH_3$, 4.11; $H_2O$, 4.49.

Neutralization Equivalent (0.5N HCl in 1:1 $CH_3CN:H_2O$):

Calcd.: 374.5. Found: 393.4.

Samples of a dihydrate, slightly over dried to contain 4.1% water (less than theoretical) rapidly picked-up water at 33%, 75% or 100% relative humidities to achieve the theoretical water content (4.6%) for the dihydrate. At 33% and 75% relative humidities, water content remained essentially constant for at least 4 days. At 100% relative humidity, the water content further rose to about 5.2, where it remained essentially constant of the next three days.

A sample of the same dihyrate, maintained at 18% relative humidity gradually lost water. At four days, the water content was 2.5% and at 12 days, 1.1%.

EXAMPLE 2

Azithromycin Powder for Oral Suspension

The following powdered ingredients were thoroughly blended:

| | |
|---|---|
| Azithromycin Dihydrate (1200 g on anhydrous basis) | 1268.5 g |
| Sucrose | 23000 g |
| Sodium phosphate tribasic dodecahydrate | 250 g |
| Sodium benzoate | 90 g |
| Hydroxypropylcellulose | 40 g |
| Xanthan gum | 40 g |
| Certified food coloring agent(s) in solid form | 3 g or as required to achieve the desired color |
| Fruit and/or vanilla flavoring agents in solid form | 440 g or as required to achieve the desired taste |

The resulting blend contains 47.75 mg of azithromycin activity per gram. Amber screw cap bottles (60 ml) are filled with 10.47 g of the blend. Prior to oral administration as a suspension, distilled water is added (25 ml) and the mixture shaken. One teaspoon (5 cc) of this mixture provides a 100 mg dose of azithromycin. Higher or lower doses are achieved by appropriate modification of the dosage volume.

EXAMPLE 3

Azithromycin Capsules (250 mg) for Oral Administration

The following ingredients were accurately weighed, combined, and blended in a suitable blender for 15 minutes.

| Hydrated azithromycin | 3360.9 g* |
|---|---|
| Anhydrous lactose | 2015.9 g |
| Corn starch | 611.0 g |

*(3250.0 g on anhydrous basis)

The blended material was milled through Fitz JT mill with a No. 2A plate (0.093") at slow speed with knives forward, the milled mixture blended for an additional 15 minutes, and weighed. The resulting milled and blended mixture (5977.2 g) was then blended for 5 minutes with a 9:1 lubricant mixture of magnesium stearate:sodium lauryl sulfate (91.65 g), the further blend slugged on a Stokes DD-2 fitted with six stations of ¾" flat faced punches, and the slugs granulated by remilling and additionally blending as specified above. Additional 9:1 lubricant (29.5 g) was blended with the resulting granulated blend (5869 g) and the material encapsulated into #0 capsules on a Zanasi RM-63 capsule machine at a fill weight of 483±23 mg to yield capsules containing no more than 275 mg and no less than the desired 250 mg of azithromycin activity.

By appropriately modifying the capsule size, the fill weight and the proportion of azithromycin in the blend, capsules containing 100 mg, 125 mg, 375 mg or 500 mg of azithromycin activity are prepared.

4"-Epi-azithromycin, 4"-amino-4"-deoxy-azithromycin and 4"-epi-4"-amino-4"deoxy-azithromycin capsules are prepared in like manner, substituting in equal weight of the active ingredient (corrected for potency as free base) for azithromycin.

EXAMPLE 4

Azithromycin Tablets (250 Mg) for Oral Administration

The following ingredients were accurately weighed, combined and blended in a suitable blender for 30 minutes:

| Azithromycin dihydrate | 14245.0 g* |
|---|---|
| Dibasic calcium phosphate | 22205.0 g |
| AC-DI-SOL | 1620.0 g |
| Magnesium stearate | 1242.7 g |

*(13,485.0 g on an anhydrous basis)

The blend was milled in a Fitzpatrick D comminutor fitted with a No. 3 plate (0.125") with knives forward at 3600 rpm, then blended for an additional 30 minutes. To the resulting milled blend (39,192 g) was added an additional 783.8 g of magnesium stearate and blending continued for 5 minutes. The mixture was then slugged according to the preceding example, and remilled as immediately above, and blended for 5 minutes. Additional magnesium stearate (394.5 g) was added to the resulting granulated blend (39,445 g), blending was continued for 5 minutes, and the mixture tableted on a Killian tableting machine with forced feeder and 32"×⅝" upper and lower oval shaped punches, each tablet having a weight of 787 mg±37 mg, each containing no less than 250 mg and no more than 275 mg of azithromycin activity.

EXAMPLE 5

Azithromycin for I.V. or I.M. Injection

In a sterile environment and using sterile, particle free equipment and components, 10,949 g of water for injection was placed in a compounding flask. Anhydrous citric acid, 494.4 g was added and dissolved with agitation. In a separate flask 310 g of sodium hydroxide was dissolved in 690 g of water. A portion of the latter (755 g) was used to adjust the pH of the citric acid from 1.63 to 5.09±0.02. Azithromycin dihydrate 670.0 g (equivalent to 642.5 g of anhydrous base) was added, and the mixture adjusted to pH 6.60±0.1 with 4.0 g additional of the sodium hydroxide solution. Water (6076.5 g) was added to bring the resulting solution to a final weight of 18,948.9 g. If desired, the solution is sterile filtered at this stage, using a millipore filter. Using a filling machine, 50 ml flint type vials were each filled with 15.06±0.45 g of this solution, loosely stoppered with gray teflon stoppers, and freeze dried to yield stoppered vials each containing 51±1.5 mg of azithromycin activity in the form of freeze dried solids. Prior to i.m. or i.v. injection, water for injection (10 ml) is added by injection by syringe through the stopper, and the freeze dried solids redissolved by shaking. Virtually the entire contents of the vial is taken up into the syringe and injected either i.v. or i.m.

PREPARATION 1

Hygroscopic Azithromycin Monohydrate

Substantially following the methylation procedure of Kobrehel et al., U.S. Pat. No. 4,517,359; and the crystallization procedure of Bright, U.S. Pat. No. 4,474,768; 9-deoxo-9a-aza-9a-homoerythromycin A (previously called 11-aza-10-deoxo-10-dihydroerythromycin A; 100 g, 0.218 mol) was dissolved with stirring in 400 ml $CHCl_3$. Formic acid (98%; 10.4 ml, 0.436 mol) and formaldehyde (37%; 16.4 ml, 0.349 mol) were added over 4-5 minutes, and the mixture heated at reflux for 20 hours. The mixture was cooled to ambient temperature, diluted with 400 ml $H_2O$ and adjusted to pH 10.5 with 50% NaOH. The aqueous layer was separated and extracted 2×100 ml with fresh $CHCl_3$. The organic layers were combined, stripped in vacuo to 350 ml, twice diluted with 450 ml of ethanol and restripped to 350 ml, and finally diluted with 1000 ml $H_2O$ over a 1 hour period, pausing for 15 minutes as a slurry began to develop after the addition of about 250 ml of $H_2O$. Title product was recovered by filtration and dried in air at 50° C. for 24 hours, 85 g; mp 136° C.; differential thermal analysis (heating rate 20° C./minute) shows an endotherm at 142° C.; thermal gravimetric analysis (heating rate 30° C./minute) shows a 2.6% weight loss at 100° C. and a 4.5% weight loss at 150° C.; water content 3.92%; ethanol content 1.09%.

Anal. Calcd. for $C_{38}H_{72}N_2O_{12}$ (corrected for ethanol and water content):

C, 58.46; H, 9.78; N, 3.74; Alkoxy, 4.67. Found: C, 58.40; H, 9.29; N, 3.50; Alkoxy, 4.52.

A sample of the monohydrate (having a water content of 3.2%) was maintained at 18% relative humidity for 14 days. The sample lost water over the first 24 hours to yield monohydrate having the theoretical water content (2.35%). The water content then remained substantially constant over 14 days, a value of 2.26% being recorded at 14 days.

At 33% relative humidity the water content of a sample of the same monohydrate rapidly rose to 5.6% where it remained substantially steady for at least three days. Similarly at 75% and 100% relative humidity, the water content rose rapidly, but was now maintained at even higher levels, 6.6% and 7.2%, respectively, for at least 3 days.

I claim:

1. A method of treating or preventing an infection in a mammal due to a strain of *Toxoplasma gondii* species which comprises administering to said mammal an anti-*Toxoplasma gondii* species effective amount of:
   azithromycin;
   4"-epi-azithromycin;
   4"-amino-4"-deoxy-azithromycin; or
   4"-epi-4"-amino-4"-deoxy-azithromycin;
   or a pharmaceutically acceptable salt thereof.

2. A method of claim 1 which comprises administering azithromycin, or a pharmaceutically acceptable salt thereof.

3. A method of claim 1 which comprises administering 4"-epi-azithromycin or a pharmaceutically acceptable salt thereof.

4. A method of claim 1 which comprises administering 4"-amino-4"-deoxy-azithromycin or a pharmaceutically acceptable salt thereof.

5. A method of treating or preventing an infection in a mammal due to a strain of *Toxoplasma gondii* species which comprises administering to said mammal an anti-*Toxoplasma gondii* species effective amount of azithromycin dihydrate.

* * * * *